United States Patent [19]

Lee

[11] Patent Number: 5,081,261

[45] Date of Patent: Jan. 14, 1992

[54] 4-(1-HYDROXY-2-N-SUBSTITUTED SULFONAMIDO) ETHYL-5-HYDROXY-2(5H)-FURANONES AND 4-(N-SUBSTITUTED SULFONAMIDO)-2-ETHENYL-5-HYDROXY-2(5H)-FURANONES AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 498,337

[22] Filed: Mar. 23, 1990

[51] Int. Cl.[5] .......................................... C07D 307/60
[52] U.S. Cl. ................................... 549/222; 544/229; 544/337; 544/379; 544/383; 549/214; 549/313; 549/318
[58] Field of Search ........................ 549/222, 313, 318

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,390,724 | 6/1983 | Martel et al. | 549/313 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |

FOREIGN PATENT DOCUMENTS

| | | | |
|---|---|---|---|
| 133376 | 2/1985 | European Pat. Off. | |
| 209274 | 1/1987 | European Pat. Off. | |
| 295056 | 6/1987 | European Pat. Off. | |
| 0369811 | 5/1990 | European Pat. Off. | 549/313 |
| 0369813 | 5/1990 | European Pat. Off. | 549/318 |

OTHER PUBLICATIONS

Bonjouklian et al., Chemical Abstracts, vol. 106, 156260c, p. 670 (1987).
Reynolds et al., J. Am. Chem. Soc., 110, pp. 5172–5177 (1988).
Tocanne et al., Chemical Abstracts 69 76581k, p. 7146 (1968).
Deems et al., Biochimica et Biophysica Acta, 917, pp. 258–268 (1987).
Scheuer et al., Journal of the American Chemical Society 100:1, p. 307 (Jan. 4, 1978).
Graziano et al., Chemical Abstracts 107 (1987), 236559t.
Negishi et al., J. Org. Chem 45, pp. 5223–5225, (1980).

*Primary Examiner*—C. Warren Ivy
*Assistant Examiner*—James H. Turnipseed
*Attorney, Agent, or Firm*—Gabor L. Szekeres; Martin A. Voet; Robert J. Baran

[57] ABSTRACT

Compounds of Formula 1, and of Formula 2,

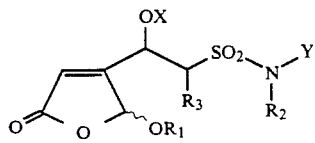

Formula 1

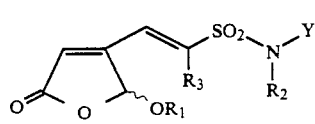

Formula 2 in which $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is H, alkyl of 1 to 20 carbons, phenyl, or substituted phenyl; $R_2$ is H, alkyl of 1 to 20 carbons, or $R_2$ and Y jointly represent a heterocycle which incorporates the sulfonamide nitrogen in the ring as a heteroatom; $R_3$ is H or alkyl of 1 to 20 carbons; X is H, $R_4$, $CO-R_4$, $CO-O-R_4$, $CO-NH-R_4$, $CO-N-(R_4)_2$, $PO(OR_4)_2$ or $PO(OR_4)R_4$, and $R_4$ independently is H, phenyl, substituted phenyl, alkyl of 1 to 20 carbons or is alkyl of 1 to 20 carbons substituted with a hydroxyl, alkoxy, substituted amino, thioalkoxy, with a $O-COR_4^*$ group or with a $COR_4^*$ group where $R_4^*$ is H, lower alkyl, OH, $OR_4^{}$, $NH_2$, $NHR_4^{}$ or $N(R_4^{})_2$ group where $R_4^{}$ independently is H or lower alkyl, with the proviso that when X is $CO-O-R_4$ or is $CO-NH-R_4$ then $R_4$ is not hydrogen, and Y is H, phenyl or substituted phenyl, or alkyl of 1 to 20 carbons, or is alkyl of 1 to 20 carbons substituted with a hydroxyl, alkoxy, substituted amino, thioalkoxy, $O-PO(OR_5)_2$, $O-PO(OR_5)R_5$, $O-SO_3H$, $O-SO_2R_5$, $O-COR_5$, or $COR_5$ group where $R_5$ is H, lower alkyl, OH, $OR_5^*$, $NH_2$, $NHR_5^*$ or $N(R_5^*)_2$ group where $R_5^*$ is lower alkyl, or $R_2$ and Y jointly represent a heterocycle which incorporates the sulfonamide nitrogen in the ring as a heteroatom, with the proviso that when Y is an alkyl substituted with $O-PO(OR_5)_2$ or with $O-PO(OR_5)R_5$ then $R_5$ is not OH, are disclosed. The compounds possess anti-inflammatory activity.

46 Claims, No Drawings

4-(1-HYDROXY-2-N-SUBSTITUTED SULFONAMIDO) ETHYL-5-HYDROXY-2(5H)-FURANONES AND 4-(N-SUBSTITUTED SULFONAMIDO)-2-ETHENYL-5-HYDROXY-2(5H)-FURANONES AS ANTI-INFLAMMATORY AGENTS

BACKGROUND OF THE INVENTION

1. Field of the Invention

The present invention is directed to novel 4-(1-hydroxy-2-N-substituted sulfonamido)ethyl-5-hydroxy-2-(5H)-furanones and 4-(N-substituted sulfonamido)-2-ethenyl-5-hydroxy-2(5H)-furanones which are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., *Tetrahedron Letters* 21:1611–1614 (1980)] which has anti-inflammatory, immunosuppressive and analgesic properties. Manoalide (Compound 1) the structure of which is shown below, includes a 5-hydroxy-2(5H)-furanone moiety, attached in the 4-position of the furanone ring to the rest of the molecule. Certain analogs of manolide, such as seco-manoalide (Compound 2) and dehydro-seco-manoalide (Compound 3) also have anti-inflammatory activity. For further description of the biological activity of manoalide and some of its derivatives reference is made to U.S. Pat. No. 4,447,445 and to European Patent Application No. 0133376 (published on Feb. 20, 1985).

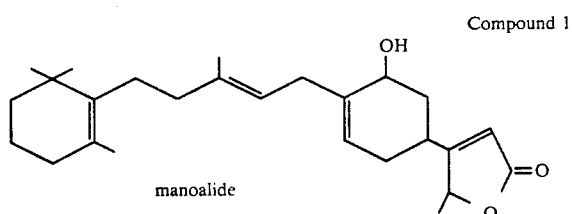

manoalide Compound 1

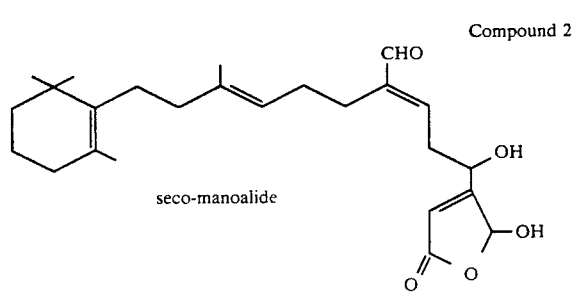

seco-manoalide Compound 2

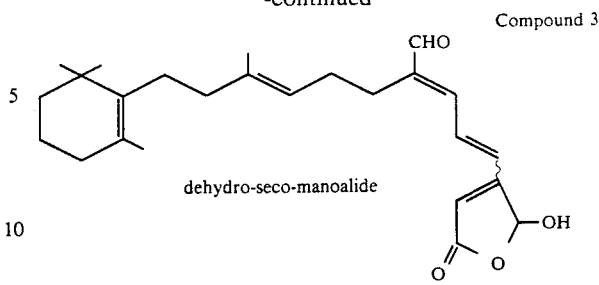

dehydro-seco-manoalide Compound 3

Synthetic analogs of manoalide, particularly analogs having various substituents on the furanone moiety of manoalide, are described in several applications for U.S. patents by the same inventor as in the present application, the following of which have been allowed and are expected to issue as U.S. Pat.:

U.S. Ser. No. 259,225 filed on Oct. 18, 1988, now U.S. Pat. No. 4,935,530;

U.S. Ser. No. 281,126 filed on Dec. 7, 1988, now abandoned.

Published European Patent Application No. 0 295 056 discloses 4-substituted 5-hydroxy-2-(5H)-furanones having antiinflammatory, immunosuppressive and antiproliferative activity where the substituents in the 4 position are a variety 1-hydroxyalkyl, 1-acyloxy-alkyl and 1-carbamoyloxy-alkyl groups.

SUMMARY OF THE INVENTION

The present invention covers compounds of Formula 1, and of Formula 2,

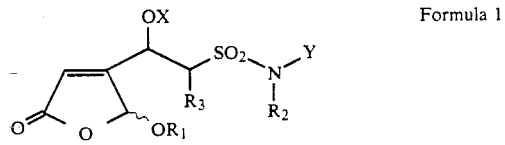

Formula 1

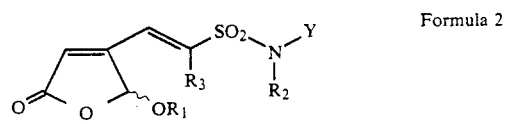

Formula 2 in which $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is H, alkyl of 1 to 20 carbons, phenyl, or substituted phenyl; $R_2$ is H, alkyl of 1 to 20 carbons, or $R_2$ and Y jointly represent a heterocycle which incorporates the sulfonamide nitrogen in the ring as a heteroatom;

$R_3$ is H or alkyl of 1 to 20 carbons;

X is H, $R_4$, $CO-R_4$, $CO-O-R_4$, $CO-NH-R_4$, $CO-N-(R_4)_2$, $PO(OR_4)_2$ or $PO(OR_4)R_4$, and $R_4$ independently is H, phenyl, substituted phenyl, alkyl of 1 to 20 carbons or is alkyl of 1 to 20 carbons substituted with a hydroxyl, alkoxy, substituted amino, thioalkoxy, with a $O-COR_4^*$ group or with a $COR_4^*$ group where $R_4^*$ is H, lower alkyl, OH, $OR_4^{}$, $NH_2$, $NHR_4^{}$ or $N(R_4^{})_2$ group where $R_4^{}$ independently is H or lower alkyl, with the proviso that when X is $CO-O-R_4$ or is $CO-NH-R_4$ then $R_4$ is not hydrogen;

Y is H, phenyl or substituted phenyl, or alkyl of 1 to 20 carbons, or is alkyl of 1 to 20 carbons substituted with a hydroxyl, alkoxy, substituted amino, thioalkoxy, O—PO(OR$_5$)$_2$, O—PO(OR$_5$)R$_5$, O—SO$_3$H, O—SO$_2$R$_5$, O—COR$_5$, or COR$_5$ group where R$_5$ is H, lower alkyl, OH, OR$_5$*, NH$_2$, NHR$_5$* or N(R$_5$*)$_2$ group where R$_5$* is lower alkyl, or R$_2$ and Y jointly represent a heterocycle which incorporates the sulfonamide nitrogen in the ring as a heteroatom, with the proviso that when Y is an alkyl substituted with O—PO(OR$_5$)$_2$ or with O—PO(OR$_5$)R$_5$ then R$_5$ is not OH.

The present invention also covers salts of the above-defined compounds, formed with pharmaceutically acceptable acids or bases, as applicable.

In a second aspect the present invention relates to pharmaceutical formulations comprising one or more compounds of Formula 1 or one or more compounds of Formula 2 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

Reaction Scheme 1

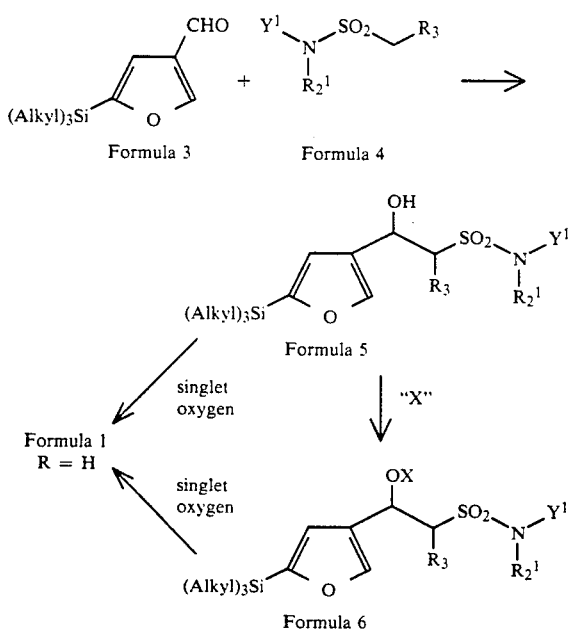

Reaction Scheme 2

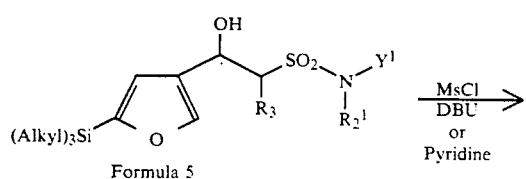

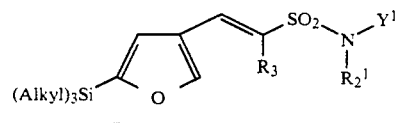

Formula 7

↓ singlet oxygen

Formula 2
R$_1$ = H

In still another aspect, the present invention relates to the processes of making the compounds of Formula 1, and the compounds of Formula 2. These processes, shown in general terms on Reaction Scheme 1 for the compounds of Formula 1 and on Reaction Scheme 2 for the compounds of Formula 2, involve the reaction of a 5-trialkylsilyl-3-furaldehyde (Formula 3, "alkyl" has 1 to 10 carbons) with a compound of the Formula 4 where R$_3$ is defines as in connection with Formula 1, and Y' and R$_2$' represent either the Y and R$_2$ groups defined in connection with Formula 1, or such suitable synthetic precursors or suitably protected derivatives of the Y and R$_2$ groups which can be readily converted in reaction steps known to a synthetic chemist or ordinary skill in the art, into the desired Y and R$_2$ groups of Formula 1 and of Formula 2, as applicable, respectively.

Thus, the 5-trialkylsilyl-3-furaldehyde of Formula 3 is reacted with the compound of Formula 4 in the presence of strong base, such as lithium diisopropylamide (LDA) to provide the 4-[1-hydroxy-2-(N-substituted-sulfonamido)]ethyl-2-trialkylsilylfuran derivatives of Formula 5. The 4-[1-hydroxy-2-(N-substituted-sulfonamido)]ethyl-2-trialkylsilylfuran derivatives (Formula 5) are then reacted with appropriate reagents in one or more reaction steps to introduce the X substituent into the hydroxy function of the side chain of the 2-trialkylsilylfuran molecule, and, if applicable, to convert the Y' and R$_2$' groups into the respective Y and R$_2$ substituents on the sulfonamide moiety of the molecule (R$_2$, X and Y having been defined in connection with Formula 1). The resulting X and Y substituted 4-[1-hydroxy-2-(N-substituted-sulfonamido)]ethyl-2-trialkylsilylfuran derivatives (Formula 6) are reacted with "singlet oxygen" to provide the compounds of Formula 1, where R$_1$ is hydrogen. The intermediates of Formula 5 (where X=H) can also be converted by reaction with singlet oxygen into the compounds of Formula 1. In the latter case the alpha hydroxyl function in the side chain of the compound of Formula 1 is unsubstituted (X=H). When it is desired to substitute (acylate, phosphorylate alkylate or the like) the 5-hydroxy function of the compounds of Formula 1, an R$_1$ group (as defined in connection with Formula 1) can be introduced into the 5-hydroxy-2-(5H)-furanone compound by conventional means.

The compounds of Formula 2 can be prepared from the intermediates of Formula 5 by introduction of a leaving group to the hydroxyl function on the side chain in the furan molecule, followed by an elimination reaction with can occur in the presence of base. The resulting 4-[2-(N-substituted-sulfonamido-2-ethenyl)]-2-trialkylsilylfuran derivatives (Formula 7, Reaction Scheme 2) are reacted with "singlet oxygen" to provide the compounds of Formula 2, where R$_1$ is hydrogen. As in the case of the compounds covered by Formula 1, when it is desired to substitute (acylate, alkylate or the like) the 5-hydroxy function of the compounds of Formula 2, an $R_1$ group (as defined in connection with Formula 2) can be introduced into the 5-hydroxy-2(5H)-furanone compound by conventional means.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, preferred amides are the mono- and di-substituted amides derived from the saturated aliphatic radicals of ten or fewer carbon atoms, or the cyclic or saturated aliphatic-cycle radicals of 5 to 10 carbon atoms.

Some of the compounds of the invention (Formula 1) contain a chiral center at the alpha carbon in the side chain on the 4-position of the furan ring. Certain compounds of the invention may contain one or more additional chiral centers. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of anantiomers in 1:1 or other ratios. Alternatively, each diastereomeric compound may be sterically and optically pure. However, all of the above-noted forms, including optically pure enantiomers and mixtures thereof as well as all diastereomers are within scope of the present invention.

Some of the compounds of the invention (Formula 2) may have cis and trans stereoisomers. The scope of the invention includes both pure stereoisomers, as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and Formula 2 and with respect to the 5-position of the furanone moiety, those where the substituent is hydroxy or acetoxy ($R_1$ is H or $CH_3CO$).

With respect to the $R_3$ substituent on the beta carbon in the side chain (in the 4-position) of the furanone moiety, the preferred compounds of the invention are those where $R_3$ is hydrogen. These compounds are, generally speaking, made by the process of Reaction Schemes 1 and 2, employing an N-substituted-methanesulfonamide as the reagent of Formula 4.

With respect to the $R_2$ substituent on the sulfonamide nitrogen, the preferred compounds of the invention are those where $R_2$ is hydrogen, or where $R_2$ and Y jointly comprise a heterocycle which incorporates the sulfonamide nitrogen as a heteroatom. In addition to mono-substituted sulfonamides ($R_2=H$) further preferred compounds in this regard are those where $R_2$, Y and the sulfonamide nitrogen jointly comprise a piperazine ring.

With respect to the Y substituent on the sulfonamide nitrogen, the preferred compounds of the invention are those where Y is alkyl, more preferably straight chain alkyl, and still more preferably "long chain" alkyl, for example of 7 to 20 carbon atoms. Also preferred are compounds where Y is straight chain alkyl substituted with a terminal OH, dialkylamino, carboxy, or with a phosphate-oxy group (in Formula 1 and in Formula 2 Y is alkyl substituted with OH, $N(R_5^*)_2$ groups, or Y is alkyl substituted with CORgroup where $R_5$ is OH, or Y is alkyl substituted with $O-PO(OR_5)_2$ group where $R_5$ is alkyl or hydroxyl. Also preferred are compounds where Y is substituted phenyl, more preferably carboxy substituted phenyl.

Still with reference to Formula 1 and Formula 2, as applicable, and with respect to the X substituent on the alpha hydroxyl function in the side chain of the furanone molecule, the preferred compounds of the invention are those where X is hydrogen, or an acyl group, preferably an acyl group derived from an alkanoic acid having a straight alkyl chain, or an acyl group derived from a straight chain alpha, omega dicarboxylic acid. Still more specifically in this regard, compounds are more preferred where X is $COCH_3$, $CO(CH_2)_{10}CH_3$, or $CO(CH_2)_3COOH$. Compounds are also preferred where the alpha hydroxyl function is converted into a carbamate, more preferably into a phenyl-carbamate, derivative (X is $CONHC_6H_5$. The most preferred compounds of the invention are those listed just below with reference to Formula 8 and Formula 9, or by full chemical name:

Compound 4: 4-[2-(N-dodecylsulfonamido)]-2-ethenyl-5-hydroxy-2(5H)-furanone;

Formula 8, Compound 5: $R_6=H$, $R_7=CH_3(CH_2)_{11}$;

Formula 8, Compound 6: $R_6=COCH_3$, $R_7=CH_3(CH_2)_{11}$;

Formula 8, Compound 7: $R_6=CO(CH_2)_3COOH$, $R_7=CH_3(CH_2)_{11}$;
Formula 8, Compound 8: $R_6=CO(CH_2)_{10}CH_3$, $R_7=(CH_2)_3OH$;
Formula 8, Compound 9: $R_6=CO(CH_2)_{10}CH_3$, $R_7=(CH_2)_2COOH$;
Formula 8, Compound 10: $R_6=CO(CH_2)_{10}CH_3$, $R_7=(CH_2)_3OPO(OEt)_2$;
Formula 8, Compound 11: $R_6=CO(CH_2)_{10}CH_3$, $R_7=(CH_2)_3OPO(OH)_2$;
Formula 8, Compound 12: $R_6=CO(CH_2)_{10}CH_3$, $R_7=(CH_2)_2N(CH_3)_2$;
Formula 8, Compound 13: $R_6=CO(CH_2)_{10}CH_3$, $R_7=$ para-carboxyphenyl ($C_6H_4COOH$);
Formula 9, Compound 14: $R_6=H$, $R_8=CH_3$;
Formula 9, Compound 15: $R_6=CO(CH_2)_{10}CH_3$, $R_8=CH_3$;
Formula 9, Compound 16: $R_6=CO(CH_2)_{10}CH_3$, $R_8=CH_3$, salt with $CH_3I$ (quaternary amine);
Formula 9, Compound 17: $R_6=CONHC_6H_5$, $R_8=CH_3$.

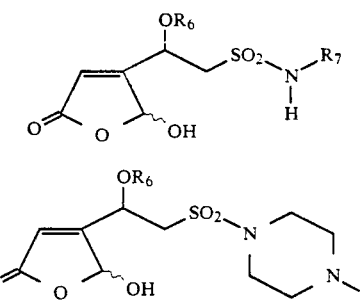

Formula 8

Formula 9

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modifications of calcium homeostasis is expected to have application in diseases of the nervous system involving modification of membrane lipids or transmitter release (Parkinson's, Alzheimer's), diseases of the cardiovascular system involving application or cardiac or vascular smooth muscle contractility and platelet aggregation (hypertension, cardiac infarction and atherosclerosis), diseases of the gastrointestial tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administrated to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administration topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
|---|---|
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
|---|---|
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5-10 mm trypsin-EDTA treatment whereas GH$_3$ cells were treated 2 to 5 min with a 1% pancreatin solution. Cells were immediately washed twice in a 20 mM HEPES buffer (pH 7.4) containing 120 mM NaCl, 6 mM KCl, 1 mM MgSO$_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. [Ca$^{2+}$]i was calculated using the following formula:

$$[Ca^{2+}]_i = 220 \times \frac{F - F_{min}}{F_{max} - F}$$

All fluorescence values were measured relative to the EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and Ca$^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900-904].

Inhibition of Phospholipase A$_2$

The effect of compounds of this invention on bee venom phospholipase A$_2$ is determined by the following procedure:

a. Bee venom phospholipase A$_2$ in 10 uM HEPES (pH 7.4) with 1 mM CaCl$_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5M H$_2$SO$_4$ (40:10:1; v:v:v:).

f. 2.0 ml n-heptane and 1.0 ml H$_2$O added; mixture centrifuged.

g. 2.0 ml n-heptane removed and treated with 200-300 mg of silica gel HR60.

h. Samples centrifuged; 1 ml of n-heptane SN removed and added to 10 ml scintillation fluid.

i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587-593 (1987).

SPECIFIC EMBODIMENTS

The compounds of the present invention can be made by the synthetic chemical pathways which are illustrated here in general terms, and in the specific examples as well. The synthetic chemist will readily appreciate that the conditions described here in general terms, and specifically, can be generalized to any and all compounds represented by Formula 1 or by Formula 2, as applicable. Furthermore, the synthetic chemist will readily appreciate that the herein described synthetic steps may be varied or adjusted by those skilled in the art without departing from the scope and spirit of the invention.

The compounds of the invention (Formula 1) are prepared in accordance with the generalized steps outlined in Reaction Scheme 1. More specifically, compounds of the invention where the sulfonamido nitrogen is mono-substituted and the side chain on the furanone molecule contains two carbons (in Formula 1 and in Formula 2 $R_2$ and $R_3$ are hydrogen) are prepared as shown in Reaction Scheme 3. Thus, a 2-triethylsilyl-4-furaldehyde (Compound 18) is reacted with an N-substituted methanesulfonamide of Formula 10 of strong base, such as lithium diisopropylamide (LAD) in an inert solvent, such as cyclohexane, tetrahydrofuran (or the like). This reaction is preferably conducted at low temperature (preferably at approximately $-78°$ C.) under a protective blanket of argon or other inert gas. In Reaction Scheme 3 the Y' group represents the substituent Y as defined in connection with Formula 1, or such synthetic precursor or protected derivative of Y which can be readily converted into the Y group by such synthetic steps which are well known to a synthetic chemist of ordinary skill. In this regard it will be readily appreciated by those skilled in the art, that certain functionalities in the Y group, such as an OH group, are not generally compatible with the reaction between 2-triethylsilyl-4-furaldehyde (Compound 18) and the N-substituted methanesulfonamide of Formula 10 occurring in the presence of strong base, and accordingly such functionalities must be appropriately protected, or introduced into the molecule after the condensation between Compound 18 and the methanesulfonamide of solvent, such as dichloromethane, preferably in the presence of an acid acceptor, such as triethylamine.

The acyl, phosphonyl, carbamoyl or like X group is introduced into the 4-[1-hydroxy-2-(N-substituted-sulfonamido)]ethyl-2-triethylsilylfuran derivatives of Formula 11 by reaction with a reagent represented by X'-L, where L is a leaving group and X' is either the same as X, or X' represents such a functionality, which in a reaction with the compounds of Formula 11 provides the X-substituted derivative of Formula 13. The L leaving group is usually halogen, and in most cases X' is the same radical as X. Typically, and by way of example, when the substituent on the alpha hydroxy group is acyl, then X'-L is an acid chloride; X'-L can also represent an acid anhydride. When the substituent on the alpha hydroxy group is a phosphonic acid residue then X'-L typically is a phosphinyl chloride, although other activated forms of phosphonic acids can also be used. Alternatively, to form an ester on the alpha hydroxy group, a condensation reaction with a suitable acid of the formula $R_4$-COOH can be conducted in the presence of dicyclohexylcarbodiimide and 4-dimethylaminopyridine ($R_4$ defines as in connection with Formula 1). In this latter situation L stands for OH.

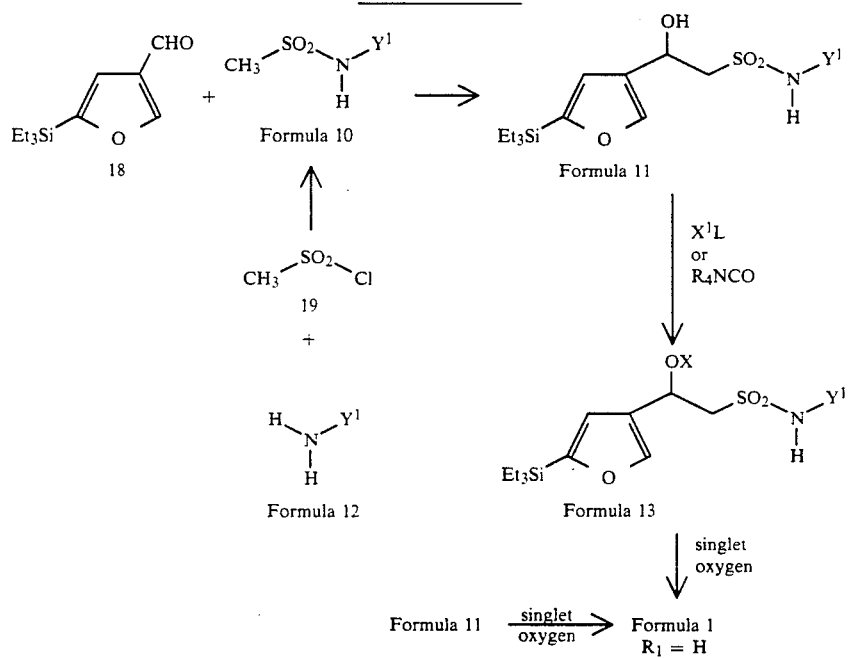

Reaction Scheme 3

Formula 10 has already taken place.

Referring still to Reaction Scheme 3, one starting material of the reaction, 2-triethylsilyl-4-furaldehyde (Compound 18) can be made in accordance with several procedures known in the chemical literature. The preferred method for the synthesis of Compound 18, however, is described in the application for United States Letters Patent Ser. No. 259,225, filed on Oct. 18, 1988, now U.S. Pat. No. 4,935,530, and assigned to the same assignee as the present application. The process for the synthesis of this important starting material is also described here in detail in the ensuing section of Specific Examples. The other reagent, the N-substituted methanesulfonamide of Formula 10 is, generally speaking, prepared from commercially available methansulfonyl chloride and an amine of Formula 12, in a suitable inert Still referring to Reaction Scheme 3, the alpha-hydroxyl group of the compounds of Formula 11 can also be reacted with a suitable chloroformate of the formula Cl—CO—$OR_4$ ($R_4$ is defined as in Formula 1) so as to form a carbonate on the alpha hydroxy group. In order to form a carbamate derivative on the alpha hydroxy group, the intermediates of Formula 11 are reacted with an isocyanate derivative of the formula $R_4$—NCO ($R_4$ is defined as in Formula 1).

In order to obtain the desired biologically active novel compounds of Formula 1, the compounds of Formula 11 and also the compounds of Formula 13 are reacted with singlet oxygen. As a result of this reaction step, the trialkylsilyl (preferably triethylsilyl) group is "removed" from the furan molecule, an oxo function is introduced into the 2-position and a hydroxy function is introduced into the 5-position. This reaction is indicated on Reaction Scheme 3 to yield compounds of Formula 1 where $R_1$ is hydrogen. In the event, substitution on the 5-hydroxy group is desired, this can be accomplished with conventional means.

Referring back again to the reaction of the 2-triethylsilyl intermediates of Formula 11 and 13, with singlet oxygen, the conditions of these reactions are described below in connection with several specific examples. In general terms, the reaction is preferably conducted in a mixture of water and acetone or in a mixture of water and tetrahydrofuran in the presence of an initiator, preferably Rose Bengal dye (preferably polymer bounded), which is added to the reaction mixture. The reaction mixture and vessel is flushed with oxygen and the reaction is conducted at low temperature, preferably at approximately 0° C., under a constant positive pressure of oxygen for a number of hours, typically 1 to 6 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

In the event the Y' group of Formula 11 requires chemical modification to provide the desired Y group (such as removal of a protecting group, or other modification) such synthetic modification is typically and preferably accomplished before reaction of the respective intermediate with singlet oxygen.

to provide the sulfonamide of Formula 15. In Formula 14 and 15 the Y' and $R_2'$ groups represent groups which, jointly with the sulfonamido nitrogen, form the desired heterocycle. The methanesulfonamide of Formula 15 is thereafter reacted with 2-triethylsilyl-4-furaldehyde (Compound 18) in a manner similar to the like reaction described in connection with Reaction Scheme 3, to give the 4-[1-hydroxy-2-(N-substituted-sulfonamido)]ethyl-2-triethylsilylfuran derivatives of Formula 16. When desired, the X substituent is introduced into the molecule by reaction with a reagent X'-L or with an isocyanate $R_4NCO$, in reactions similar to the corresponding reactions described in connection with Reaction Scheme 3. The 4-[1-hydroxy-2-(N-substituted-sulfonamido)]ethyl-2-triethylsilylfuran derivatives, where the alpha hydroxyl group is substituted with X are represented by Formula 17 in Reaction Scheme 4. The triethylsilylfuran compounds of Formula 16 as well as of Formula 17 provide, upon treatment with singlet oxygen, the compounds of Formula 1, where the 5-hydroxyl group is unsubstituted ($R_1$ is hydrogen), and where the sulfonamido nitrogen is part of a heterocyclic ring. An $R_1$ substituent, such as an acetyl group can be introduced by conventional means.

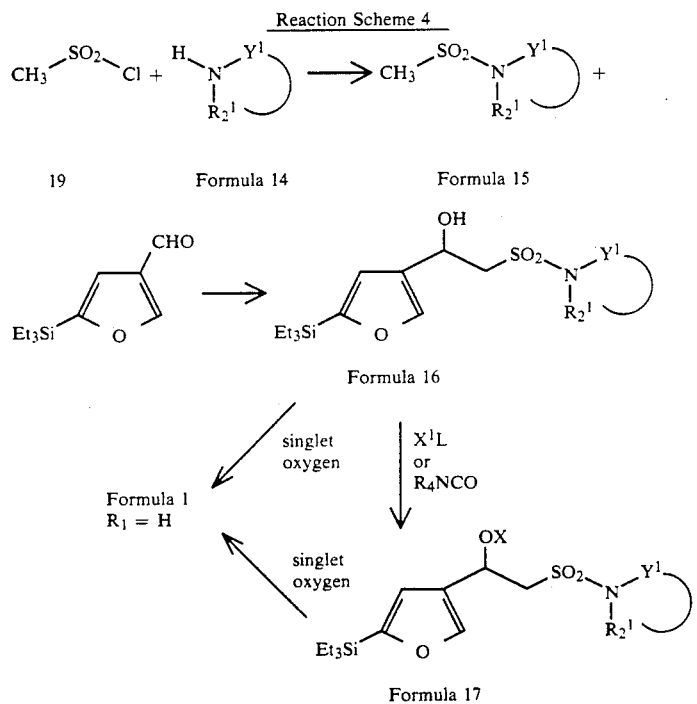

Reaction Scheme 4 discloses a general synthetic route to the compounds of the invention of Formula 1, where the sulfonamido nitrogen is included in a heterocycle (such as N-methylpiperazine) so that in Formula 1 Y, $R_2$ and the sulfonamido nitrogen jointly form the heterocycle. In accordance with this generalized reaction sequence, methanesulfonyl chloride (Compound 19) is reacted with a heterocycle having at least one nucleophilic nitrogen in the ring (Formula 14) in an inert solvent (such as tetrahydrofuran) and preferably in the presence of an acid acceptor (such as triethylamine)

Reaction Scheme 5

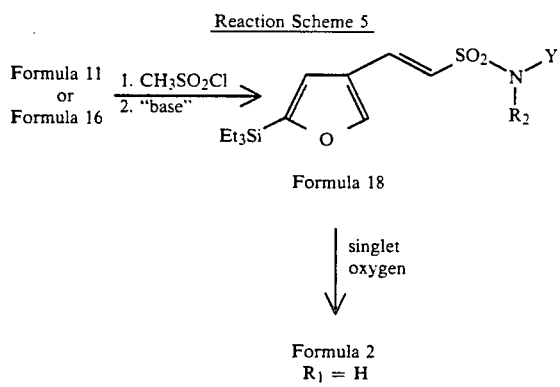

Formula 11
or
Formula 16

1. CH₃SO₂Cl
2. "base"

Formula 18

| singlet oxygen

Formula 2
$R_1 = H$

Referring now to Reaction Scheme 5, a general synthetic route to compounds of Formula 2 is disclosed. In accordance with this scheme, either the intermediate of Formula 11, or the intermediate of Formula 16 is reacted with methanesulfonyl chloride (Compound 19) or with an equivalent reagent, to place a good leaving group such as "methanesulphonyl" on the alpha hydroxyl function. The resulting methanesulfonyl derivative is treated with base, resulting in elimination of the methanesulfonyloxy group, and formation of the compounds of Formula 18. The methanesulfonylation and elimination reactions are preferably performed without isolation of the mesylate intermediate, and pyridine or 1,8-diazabicyclo[5,4,0]undec-7-ene (DBU) can serve, for example, as the base which brings about the elimination reaction. The intermediate 2-triethylsilyl-4-(2-N-substituted sulfonamido)ethenylfurans of Formula 18 are treated with singlet oxygen to provide the compounds of Formula 2, where $R_1$ is H.

The following examples of specific compounds of the invention, and specific examples of the synthetic steps in which the compounds and certain intermediates are made, are set out to illustrate the invention, not to limit its scope.

SPECIFIC EXAMPLES

Example 1

5-Triethylsilyl-3-furaldehyde (Compound 18)

n-Butyl lithium (a 2.5M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to given an oil, which was distilled under high vacuum to give the 5-triethylsily-3-furaldehyde as a pale yellow oil, boiling point 85°–90°/0.4 torr.

IR (neat) 1680 cm⁻¹

¹H NMR (CDCl₃) 0.79 (q, 6H, J=7.3 Hz), 0.90 (t, 9H, J=7.3 Hz), 7.0 (s, 1H), 8.26 (s, 1H) and 9.95 (s, 1H).

¹³C NMR (CDCl₃) 2.9, 7.1, 117.2, 128.8, 155.6, 162.3 and 184.6.

HRMS m/e exct mass calculated for $C_{11}H_{18}O_2Si(M+)$ 210.1076, Found 210.1071.

N-Dodecylmethanesulfonamide (Compound 20)

A mixture of 1-aminododecane (5.67 g, 30 mmol), methanesulfonyl chloride (2.52 ml, 32.6 mmol) and triethylamine (4.5 ml, 32.6 mmol) in dichloromethane (30 ml) was stirred at room temperature for 14 hours. The mixture was poured into water and the layers were separated. Evaporation of the dried (magnesium sulfate) organic layer gave a solid, which after trituration with cold hexane gave the title sulfonamide. ¹HNMR(CDCl₃): 0.92 (t, 3H, J=7.1 Hz), 1.29 (br s, 18H), 1.60 (2H), 2.99 (s, 3H), 3.16 (dd, 2H, J=13.3 Hz, 6.4 Hz) and 4.25 (br, 1H). HRMS exact mass calculated for $C_{13}H_{30}NO_2 (M+H)+$ 264.1997, found 264.1993.

4-[1-Hydroxy-2-(N-dodecylsulfonamido)]ethyl-2-triethylsilylfuran (Compound 21)

Lithium diisopropylamide (a 1.5M solution in cyclohexane; 18.6 ml, 27.8 mmol) was added dropwise to a solution of N-dodecylmethanesulfonamide (Compound 20, 2.92 g, 12.7 mmol) at −78° C. under argon. After stirring for 30 minutes at −55° C., a solution of 2-triethylsilyl-4-furaldehyde (Compound 18 2.66 g, 12.7 mmol) was added. Stirring was continued at −55° C. for 14 hours and the mixture was quenched with water. Extraction (ethyl ether) and evaporation of the dried (magnesium sulfate) extracts gave an oil, which was purified by chromatography on a silica column, using 20% ethyl acetate to give the title furan. IR(CDCl₃): 3500, 3380, 1340 and 1200. ¹HNMR(CDCl₃): 0.70 (q, 6H, J=7.7 Hz), 0.83 (t, 3H, J=6.7 Hz), 0.93 (t, 9H, J=7.8 Hz), 1.26 (m, 18H), 1.49 (m, 2H), 3.02 (m, 2H), 3.21 (dd, 1H, J=14.5 Hz, 2.1 Hz), 3.40 (dd, 1H, J=14.5 Hz, 10.1 Hz), 3.77 (d, 1H, J=3.4 Hz), 5.21 (m, 2H), 6.58 (s, 1H) and 7.57 (s, 1H). ¹³CNMR(CDCl₃) 2.7, 6.8, 13.7, 22.8, 26.3, 28.9, 29.0, 29.2, 29.3, 29.8, 31.6, 43.1, 57.7, 62.4, 118.7, 126.2, 143.6 and 160.3. HRMS exact mass calculated for $C_{24}H_{47}NO_4SSi(M+)$ 473.2995, found 473.2979.

4-[1-Hydroxy-2-(N-dodecylsulfonamido)]ethyl-5-hydroxy-2(5H)-furanone (Compound 5)

A mixture of 4-[1-hydroxy-2-(N-dodecylsulfonamido)]ethyl-2-triethylsilylfuran (Compound 21, 188 mg, 0.39 mmol), water (a few drops) and Rose Bengal (5 mg) in acetone (30 ml) was exposed to singlet oxygen at 0° C. for 8 hours. The residue, after solvent removal, was purified by a silica column using 40% ethyl acetate/hexane to give the titled furnace. IR (CHCl₃): 3400, 1760 and 920. ¹HNMR(CDCl₃): 0.88 (t, 3H, J=6.7 Hz), 1.29 (m, 18H), 1.57 (m, 2H), 3.07 (m, 2H), 3.43 (br m, 1H), 3.59 (br m, 1H), 4.53 (br m, 1H), 5.11 (br m, 1H), 5.35 (br m, 1H) and 6.18 (br m, 3H). ¹³CNMR(CDCl₃): 13.9, 22.5, 26.5, 29.1, 29.2, 29.4, 29.5, 29.9, 31.8, 43.5, 54.3, 54.4, 54.5, 54.6, 63.7, 63.9, 97.9, 98.2, 114.5, 167.9, 168.6, 171.8 and 171.9.

Example 2

4-[1-Acetoxy-2-(N-dodecylsulfonamido)]ethyl-2-triethylsilylfuran (Compound 22)

A mixture of 4-[1-hydroxy-2-(N-dodecylsulfonamido)]ethyl-2-triethylsilylfuran (Compound 21, 200 mg, 0.42 mmol), acetic anhydride (1 ml) and pyridine (1 ml) was stirred at room temperature for 14 hours. The solution was diluted with ethyl ether and was washed with saturated sodium bicarbonate and water. Evaporation of the dried (magnesium sulfate) organic phase gave an oil, which was purified on a silica column using 20% ethyl acetate/hexane to give the title furan. IR(CHCl$_3$): 3385, 3280, 2905, 1725 and 1200. $^1$HNMR(CDCl$_3$): 0.71 (q, 6H, J=7.8 Hz), 0.83 (t, 3H, J=6.7 Hz), 0.93 (t, 9H, J=7.8 Hz), 1.20 (m, 18H), 1.49 (m, 2H), 3.03 (m, 2H), 2.05 (s, 3H), 3.36 (dd, 1H, J=14.8 Hz, 3.5 Hz), 3.60 (dd, 1H, J=14.8 Hz, 9.2 Hz), 4.77 (t, 1H, J=6.0 Hz), 6.27 (dd, 1H, J=9.2 Hz, 3.5 Hz), 6.58 (s, 1H) and 7.67 (s, 1H). $^{13}$CNMR(CDCl$_3$): 2.8, 6.9, 13.8, 20.8, 22.4, 26.3, 28.9, 29.1, 29.2, 29.3, 29.4, 29.9, 31.7, 43.2, 55.6, 63.3, 119.0, 122.7, 145.0, 160.7, and 170.5. HRMS exact mass calculated for $C_{26}H_{40}NO_4SSi(M+)$ 515.3101, found 515.3080.

4-[1-Acetoxy-2-(N-dodecylsulfonamido)]ethyl-5-hydroxy-2(5H)-furanone (Compound 6)

A mixture of 4-[1-acetoxy-2-(N-dodecylsulfonamido)]ethyl-2-triethylsilylfuran (Compound 22, 197 mg, 0.38 mmol), water (a few drops) and Rose Bengal (5 mg) in acetone (30 ml) was exposed to singlet oxygen at 0° C. for 8 hours. The residue, after solvent removal, was purified by a silica column using 40% ethyl acetate/hexane to give the titled furanone. IR(CHCl$_3$): 3400, 3300, 2930, 1740 and 1150. $^1$HNMR(CDCl$_3$): 0.88 (t, 3H, J=6.7 Hz), 1.30 (m 18H), 1.56 (m, 2H), 2.17 (s, 3H), 3.10 (dt, 2H, J=6.7 Hz, 6.7 Hz), 3.67 (br m, 2H), 5.22 (t, 1H, J=5.9 Hz), 5.87 (br s, 1H), 6.04 (brs, 1H), 6.27 (s, 1H) and 7.28 (br s, 1H). $^{13}$CNMR(CDCl$_3$): 13.8, 20.5, 22.4, 26.4, 28.9, 29.1, 29.3, 29.4, 29.9, 31.7, 43.3, 53.1, 64.7, 97.9, 120.8, 163.5, 170.3 and 170.4. HRMS (FAB) exact mass calculated for $C_{20}H_{35}NO_7S(M+H)^+$ 434.2214 found 434.2216.

4-[2-(N-Dodecylsulfonamide)]ethenyl]-2-triethylsilylfuran (Compound 23)

A mixture of 4-[1-hydroxy-2-(N-dodecylsulfonamido)]ethyl-2-triethylsilylfuran (Compound 21, 221 mg, 0.47 mmol), methanesulfonylchloride (Compound 19, 0.15 ml, 1.87 mmol) and pyridine (0.11 ml, 1.4 mmol) in tetrohydrofuran (2 ml) was stirred at room temperature for 14 hours. The mixture was quenched with water and was extracted with ethyl ether. Evaporation of the dried (magnesium sulfate) extracts gave an oil, which was purified by a silica column using 10% ethyl acetate/hexane to give the title furan. $^1$HNMR(CDCl$_3$): 0.77 (q, 6H, J=7.1 Hz), 0.88 (t, 3H, J=6.7 Hz), 0.99 (t, 9H, J=7.8 Hz), 1.29 (m, 18H), 1.54 (m, 2H), 3.03 (d, 2H, J=7.0 Hz, 6.5 Hz), 4.48 (m, 1H), 6.48 (d, 1H, J=15.3 Hz), 6.75 (s, 1H), 7.40 (d, 1H, J=15.3 Hz) and 7.86 (s, 1H). $^{13}$CNMR(CDCl$_3$): 2.9, 7.2, 14.1, 22.7, 26.6, 29.1, 29.3, 29.4, 29.5, 29.6, 29.8, 31.9, 43.0, 117.7, 120.5, 123.7, 132.2, 147.2, 149.1 and 161.5. HRMS exact mass calculated for $C_{24}H_{45}NO_3SSi(M+)$ 455.2889 found 455.2887.

4-[2-(N-Dodecylsulfonamido)ethenyl]-5-hydroxy-2(5H)-furanone (Compound 4)

A mixture of 4-[2-(n-dodecylsulfonamido)ethenyl]-2-triethylsilylfuran (Compound 23, 39 mg, 0.098 mmol), water (a few drops) and Rose Bengal (5 mg) in acetone (10 ml) was exposed to singlet oxygen at 0° for 3 hours. The residue, after solvent removal was purified on a silica column using 50% ethyl acetate/hexane to give the title furanone. IR(CHCl$_3$) 3300, 2920, 1750 and 1145. $^1$HNMR(CDCl$_3$): 0.88 (t, 3H, J=6.6 Hz), 1.33 (m, 18H), 1.56 (m, 2H), 3.06 (dt, 2H, J=6.9 Hz, 6.4 Hz), 4.72 (t, 1H, J=6.0 Hz), 5.10 (br s 1 H), 6.99 (d, 1H, J=15.2 Hz) and 7.27 (d, 1H, J=15.5 Hz). $^{13}$CNMR(CDCl$_3$): 13.9, 22.5, 26.4, 28.9, 29.1, 29.3, 29.4, 29.9, 31.7, 43.2, 97.4, 124.5, 128.5, 136.0, 156.7 and 169.8. HRMS exact mass calculated for $C_{18}H_{32}NO_5S(M+)$ 374.2001 found 374.2027.

4-[1-Glutaroyloxy-2-(N-dodecylsulfonamido)]ethyl-2-triethylsilylfuran (Compound 24)

Potassium bis(trimethylsilyl)amide (a 0.5M solution in toluene: 3.04 ml, 1.52 mmol) was added to a solution of 4-[1-hydroxy-2-(N-dodecylsulfonamido)]ethyl-2-triethylsilylfuran (Compound 21, 359.6 mg, 0.76 mmol) in tetrahydrofuran (20 ml) at 0° under argon. After 30 min, a solution of glutaric anhydride (260 mg, 2.28 mmol) in tetrahydrofuran (2 ml) was added. Stirring was continued for 14 hours, while the cooling bath attained room temperature. The reaction was quenched with water and was extracted with ethyl ether. Evaporation of the dried (magnesium sulfate) extracts gave an oil, which was purified by a silica column using 40% ethyl acetate/hexane to give the title furan. IR(CHCl$_3$): 3600, 2600 and 1730. $^1$HNMR(CDCl$_3$): 0.69 (q, 6H, J=7.7 Hz), 0.82 (t, 3H, J=6.7 Hz), 0.92 (t, 9H, J=7.8 Hz), 1.20 (m, 18H), 1.48 (m, 2H), 1.89 (m, 2H), 2.37 (m, 4H), 3.01 (m, 2H), 3.33 (dd, 1H J=14.7 Hz, 3.5 Hz), 3.61 (dd, 1H, J=14.7 Hz, 9.2 Hz), 5.03 (t, 1H, J=5.9 Hz), 5.27 (dd, 1H, J=9.3 Hz, 3.4 Hz), 6.56 (s, 1H) and 7.64 (s, 1H). $^{13}$CNMR(CDCl$_3$): 3.1, 7.3, 14.2, 19.7, 22.8, 26.7, 29.3, 29.5, 29.6, 29.7, 29.8, 30.0. 30.5, 32.0, 32.9, 33.3, 43.5, 56.0, 63.7, 119.3, 123.1, 145.4, 161.1, 172.7 and 179.1.

4-[1-Gluraroyloxy-2-(N-dodecylsulfonamido)]ethyl-5-hydroxy-2(5H)-furanone (Compound 7)

A mixture of 4-[1-glutaroyloxy-2-(N-dodecylsulfonamido)]ethyl-2-triethylsilylfuran (Compound 24, 295 mg, 0.5 mmol), water (a few drops) and Rose Bengal (5 mg) in acetone (10 ml) was exposed to singlet oxygen at 0° C. for 6 hours. The residue, after solvent removal, was purified by a silica column using 80% ethyl acetate/hexane to give the title furanone. IR(CDCl$_3$): 3300, 2920 and 1725. $^1$HNMC(CDCl$_3$): 0.82 (t, 3H, J=6.7 Hz), 1.22 (m, 18H), 1.49 (br m, 2H), 1.89 (br m, 2H), 2.37 (br m, 2H), 2.46 (br m, 2H), 3.02 (br m, 2H), 3.56 (br m, 2H), 5.43 (br m, 1H), 6.00 (br m, 1H), 6.08 (br s, 1H), 6.13 (s, 1H), 6.20 (br s, 1H), and 6.31 (br, 1H). $^{13}$CNMR(CDCl$_3$): 13.8, 19.2, 22.4, 26.4, 29.0, 29.1, 29.3, 29.4, 30.0. 31.7, 32.5, 43.2, 52.8, 53.8, 52.9, 53.0, 64.6, 64.7, 97.8, 97.9, 98.0, 120.6, 120.7, 163.4, 163.8, 170.7, 170.8, 172.5 and 178.0. HRMS (FAB) exact mass calculated for $C_{23}H_{39}NO_9S.Na(M+Na)^+$ 528.2255 found 528.2237.

Example 5

N-Methyl-N'-methanesulfonylpiperazine (Compound 25)

A mixture of N-methylpiperazine (3.0 g, 29.9 mmol), triethylamine (3.6 g, 35.9 mmol) and methanesulfonyl chloride (Compound 19, 4.11 g, 35.9 mmol) in tetrahydrofuran (20 ml) was stirred at 0° C. for 2 hours. The mixture was filtered and the filtrate was evaporated to dryness to give a solid. The solid was redissolved in ethyl acetate and washed with water. Evaporation of the dried (magnesium sulfate) organic phase gave the title sulfonamide. $^1$HNMR(CDCl$_3$): 2.35 (s, 3H), 2.53 (t, 4H, J=5.0 Hz), 2.79 (s, 3H) and 3.27 (t, 4H, J=5.0 Hz).

4-(1-Hydroxy-2-N'-methylpiperazylsulfonyl)ethyl-2-triethylsilylfuran (Compound 26)

A solution of N-methyl-N'-methanesulfonylpiperazine (Compound 25, 933 mg, 5.24 mmol) in tetrahydrofuran (3ml) was added to a solution of lithium diisopropylamide (5.24 mmol; prepared from 0.73 ml diisopropylamine and 2.09 ml of a 2.5M solution of n-butyl lithium) at 0° C. under argon. After 30 minutes, a solution of 2-triethylsilyl-4-furaldehyde (Compound 18, 1.0 g, 4.76 mmol) in tetrahydrofuran (2 ml) was added. Stirring was continued overnight while the cooling bath attained room temperature. The mixture was quenched with water and extracted with ethyl acetate. The organic extracts were combined, dried (magnesium sulfate) and evaporated down to give a residue. The residue was purified on a silica column using 2.5 % methanol/chloroform to give the title furan. $^1$HNMR(CDCl$_3$): 0.76 (q, 6H, J=8.0 Hz), 0.98 (t, 9H, J=8.0 Hz), 2.30 (s, 3H), 2.50 (t, 4H, J=4.9 Hz), 3.17 (dd, 1H, J=14.1 Hz, 1.7 Hz), 3.30 (dd, 1H, J=4.3 Hz, 14.1 Hz), 3.35 (br, 6H), 5.30 (d, 1H, J=9.7 Hz), 6.60 (s, 1H), and 7.64 (s, 1H). $^{13}$CNMR(CDCl$_3$): 3.1, 7.2, 45.2, 45.6, 54.4, 56.5, 61.8, 118.6, 126.4, 143.3 and 160.2. LRMS (m/e % abundance) 388 (M$^+$, 9), 371(1), 359(1), 100(20), 99(100), 97(22) and 56(12).

4-(1-Hydroxy-2-N'-methylpiperazylsulfonyl)ethyl-5-hydroxy-2(5H)-furanone (Compound 14)

A mixture of 4-(1-hydroxy-2-N'-methylpiperazylsulfonyl)ethyl-2-triethylsilylfuran (Compound 26, 100 mg, 0.26 mmol), water (a few drops) and Rose Bengal (6.5 mg) in tetrahydrofuran (10 ml) was exposed to singlet oxide at 0° C. for 3 hours. The residue, after solvent removal, was purified on a silica column using 10% methanol/chloroform to give the title furanone. $^1$HNMR(CD$_3$OD): 2.24 (s, 3H), 2.44 (t, 4H, J=5.0 Hz), 3.23 (m, 4H), 3.35 (br, 1H), 3.42 (br, 1H), 4.86 (dt, 1H, J=8.3 Hz, 2.1 Hz), 6.07 (s, 1H), and 6.22 (s, 1H).

Example 6

4-(1-Dodecanoyloxy-2-N'-methylpiperazylsulfonyl)ethyl-5-triethylsilylfuran (Compound 27)

A mixture of 4-(1-hydroxy-2-N'-methylpiperazylsulfonyl)ethyl-5-triethylsilylfuran (Compound 26, 250 mg, 0.64 mmol), dodecanoyl chloride (0.36 ml, 1.54 mmol) and triethylamine (0.22 ml, 1.54 mmol) in dichloromethane (10 ml) was stirred at room temperature for 2 days. The mixture was quenched with water and extracted with ethyl acetate. Evaporation of the dried (magnesium sulfate) extracts gave a residue, which was purified on a silica column with 60% ethyl acetate/hexane to give the title furan. $^1$HNMR(CDCl$_3$): 0.76 (q, 6H, J=8.0 Hz), 0.88 (t, 3H, J=6.9 Hz), 0.97 (t, 9H, J=8.0 Hz), 1.24 (m, 8H), 1.60 (m, 2H), 2.30 (m, 5H), 2.47 (t, 4H, J=4.9 Hz), 3.30 (m, 5H), 3.54 (m, 1H), 6.30 (dd, 1H, J=3.6 Hz, 8.9 Hz), 6.57 (s, 1H) and 7.66 (s, 1H). $^{13}$CNMR(CDCl$_3$): 3.0, 7.1, 14.0, 22.6, 24.6, 28.9, 29.1, 29.2, 29.3, 29.5, 31.8, 34.2, 45.5, 53.6, 54.4, 62.6, 118.8, 122.8, 144.7, 160.1 and 172.2.

4-(1-Dodecanoyloxy-2-N'-methylpiperazylsulfonyl)ethyl-5-hydroxy-2-(5H)furanone (Compound 15)

A mixture of 4-(1-dodecanoyloxy-2-N'-methylpiperazylsulfonyl)ethyl-2-triethylsilylfuran (Compound 27, 100 mg, 0.18 mmol), water (a few drops) and Rose Bengal (5 mg) in acetone (25 ml) was exposed to single oxygen at 0° C. for 2 hours. The residue, after solvent removal, was purified on a silica column using 5% methanol/chloroform to give the title furanone. $^1$HNMR(CDCl$_3$): 0.88 (t, 3H, J=6.9 Hz), 1.26 (m, 16H), 1.65 (m, 2H), 2.39 (s, 3H), 2.42 (dd, 2H, J=7.7 Hz, 3.5 Hz), 2.61 (br, 4H), 3.30 (br, 4H), 3.40 (d, 1H, J=8.3 Hz), 3.54 (dd, 1H, J=14.5 Hz, 3.8 Hz), 6.0 (dd, 1H, J=7.89 Hz, 4.8 Hz), 6.13 (s, 1H), and 6.28 (s, 1H). $^{13}$CNMR(CDCl$_3$): 13.8, 24.4, 28.9, 29.0, 29.1, 29.9, 29.4, 31.7, 33.8, 44.6, 45.1, 50.3, 53.9, 63.9, 101.7, 121.2, 163.0, 169.7 and 172.6.

Example 7

N'-Methyl-4-(1-dodecanoyloxy-2-N'-methylpiperazylsulfonyl)ethyl-5-triethylsilylfuran iodide (Compound 28)

A mixture of 4-(1-dodecanoyloxy-2-N'-methylpiperazylsulfonyl)ethyl-5-triethylsilylfuran (Compound 27, 100 mg, 0.18 mmol) and excess iodomethane (1ml) was stirred at room temperature for 2 days. The excess iodomethane was removed under high vacuum to give the title salt. $^1$HNMR(CDCl$_3$): 0.75 (q, 6H, J=8.0 Hz), 0.88 (t, 3H, J=6.9 Hz), 0.97 (t, 9H, J=8.0 Hz), 1.25 (m, 18H), 1.59 (m, 2H), 2.30 (t, 2H, J=7.4 Hz), 3.59 (br, 6H), 3.80 (m, 10H), 6.34 (dd, 1H, J=8.4 Hz, 3.8 Hz), 6.67 (s, 1H), and 7.91 (s, 1H).

The above iodide salt was converted to the corresponding 2(5H-furanone (Compound 16) under similar condition as in Example 1.

Example 8

4-(1-Phenylcarbamoyl-2-N'-methylpiperazylsulfonyl)ethyl-5-hydroxy-2-(5H)-furanone (Compound 17)

4-(1-Hydroxy-2-N'-methylpiperazylsulfonyl)ethyl-2-triethylsilylfuran (Compound 26) is reacted with phenyl isocyanate to give 4-(1-phenylcarbamoyl-2-N'-methylpiperazylsulfonyl)ethyl-2-triethylsilylfuran. Oxidizing this furan with oxygen using Rose Bengal as initiator gives 4-(1-phenylcarbamoyl-2-N'-methylpiperazylsulfonyl)ethyl-5-hydroxy-2(5H)-furanone (Compound 17).

Example 9

3-tert-Butyldimethylsiloxy-1-propylamine (Compound 29)

tert-Butyldimethylsilyl chloride (14.7 g, 97.5 mmol), followed by 1,8-diazabicyclo[5.4.0]undec-7-ene (14.6 ml, 97.5 mmol) was added to a solution 3-amino-1-propanol (7.45 ml, 97.5 mmol) in dichloromethane (100 ml) at 0° C. under argon. After 6 hours stirring at room temperature, the mixture was quenched with water and washed successively with 10% hydrochloric acid, saturated sodium bicarbonate solution and brine. Evaporation of the dried (magnesium sulfate) organic phase gave the title amine. $^1$(HNMR(CDCl$_3$): −0.03 (s, 6H), 0.81 (s, 9H), 1.61 (p, 2H, J=6.1 Hz), 2.20 (br, 2H), 2.75 (t, 2H, J=6.8 Hz) and 3.63 (t, 2H, J=6.12 Hz).

N-(3-tert-Butyldimethylsiloxy)propyl methanesulfonamide (Compound 30)

Triethylamine (1.16 ml, 16 mmol), followed by methanesulfonyl chloride (Compound 19, 1.48 ml, 19.2 mmol) was added to a solution of 3-tert-butyldimethylsiloxy-1-propylamine (Compound 29, 2.80 g, 16 mmol) in tetrahydrofuran (60 ml) at 0° C. under argon. After stirring at room temperature overnight, the mixture was washed successively with dilute hydrochloric acid, saturated sodium bicarbonate and brine. Evaporation of the dried (magnesium sulfate) organic phase gave the title sulfonamide. $^1$HNMR(CDCl$_3$): 0.04 (s, 6H), 0.87 (s, 9H), 1.76 (p, 2H, J=6.4 Hz), 2.91 (s, 3H), 3.24 (q, 2H, J=6.2 Hz), 3.74 (t, 2H, J=5.52 Hz) and 5.05 (br t, 1H).

4-[1-Hydroxy-2-N-(3-tert-butyldimethylsiloxy)propyl-sulfonamido]ethyl-2-triethylsilylfuran (Compound 31)

A solution of lithium diisopropylamide (5.52 mmol; prepared from 0.77 ml diisopropylamine and 5.52 mmol n-butyl lithium in 2 ml tetrahydrofuran at 0° C.) was added to solution of N-(3-tertbutyldimethylsilyloxy)-propyl methanesulfonamide (Compound 30, 703 mg, 2.62 mmol) at −78° C. under argon. After 2 hours stirring the solution was cannulated into a solution of 2-triethylsilyl-4-furaldehyde (Compound 18, 567 mg, 2.70 mmol) in tetrahydrofuran (3 ml) at −78° C. On warming to room temperature, the solution was quenched with ammonium chloride and extracted thoroughly with diethyl ether. Evaporation of the dried (magnesium sulfate) extracts gave an oil, which was purified on a silica column using 20% ethyl acetate/hexane to give the title furan. IR(CHCl$_3$): 3540, 3340 and 1320. $^1$HNMR(CDCl$_3$): 0.04 (s, 6H), 0.73 (q, 6H, J=6.8 Hz), 0.87 (s, 9H), 0.94 (t, 9H, J=7.8 Hz), 1.76 (m, 2H, J=5.4 Hz), 3.25 (m, 5H), 3.40 (dd, 1H, J=14.3 Hz, 9.9 Hz), 3.74 (t, 2H, J=5.7 Hz), 5.2 (br t+brd, 2H), 6.59 (s, 1H), and 7.62 (s, 1H). $^{13}$CNMR(CDCl$_3$): −5.8, 2.8, 6.9, 17.9, 25.7, 31.7, 41.9, 58.3, 61.9, 62.6, 118.7, 126.0, 143.7 and 160.7. HRMS exact mass calculated for C$_{21}$H$_{42}$NO$_4$SSi$_2$ (M-OH)$^+$ 460.2376, found 460.2377.

4-[1-Dodecanoyloxy-2-N-(3-tert-butyldimethylsiloxy)-propylsulfonamido]ethyl-2-triethylsilylfuran (Compound 32)

Triethylamine (0.37 ml, 2.63 mmol), followed by dodecanoyl chloride (0.64 mol, 2.76 mmol) was added to a solution of 4-[1-hydroxy-2-N-(3-tert-butyldimethylsiloxy)propylsulfonamido]ethyl-2-triethylsilylfurane (Compound 31, 563 mg, 1.25 mmol) in dichloromethane (5 ml) at 0° C. under argon. After 3.5 hours, the solution was diluted with ethyl ether and washed successively with 5% dilute hydrochloric acid, sodium bicarbonate solution and brine. Evaporation of the dried (magnesium sulfate) organic phase gave an oil, which was purified by flash chromatography on silica using 10% ethyl acetate/hexane to give the title furan. IR(CHCl$_3$): 3350, 1740 and 1340. $^1$HNMR(CDCl$_3$): 0.02 (s, 6H), 0.71 (q, 6H, J=6.8 Hz), 0.84 (t+s, 12H), 0.93 (t, 9H, J=6.8 Hz), 1.25 (br s, 16H), 1.58 (m, 2H), 1.75 (p, 2H, J=6.4 Hz), 2.30 (t, 2H, J=7.7 Hz), 3.18 (m, 2H), 3.34 (dd, 1H, J=14.8 Hz, 3.6 Hz), 3.58 (dd, 1H, J=14.8 Hz, 9.0 Hz), 3.70 (t, 2H, J=5.7 Hz), 4.90 (t, 1H, J=6.1 Hz), 6.27 (dd, 1H, J=9.0 Hz, 3.6 Hz), 6.56 (s, 1H), and 7.62 (s, 1H). $^{13}$CNMR(CDCl$_3$): −5.8, 2.8, 6.9, 13.8, 17.9, 22.4, 22.5, 24.5, 25.7, 28.9, 29.0, 29.1, 29.2, 29.4, 31.7, 32.1, 34.1, 41.4, 55.8, 61.3, 63.1, 119.1, 122.9, 144.9, 160.7 and 173.2.

4-[1-Dodecanoyloxy-2-N-(3-tert-butyldimethylsiloxy)-propylsulfonamido]ethyl-5-hydroxy-2-(5H)-furanone (Compound 33)

Singlet oxygen oxidation of 4-[1-dodecanoyloxy-2-N-(3-tert-butyldimethylsiloxy)propylsulfonamido]ethyl-2-triethylsilylfuran (Compound 32) under similar conditions as in Example 1, gives 4-[1-dodecanoyloxy-2-N-(3-tert-butyldimethylsiloxy)propylsulfonamido-ethyl-5-hydroxy-2(5H)-furanone (Compound 33).

Example 10

4-[1-Dodecanoyloxy-2-N-(3-hydroxypropyl)sulfonamido]ethyl-2-triethylsilylfuran (Compound 34)

A mixture of 4-[1-dodecanoyloxy-2-N-(3-tert-butyldimethylsiloxy)propylsulfonamido]ethyl-2-triethylsilylfuran (Compound 32, 446 mg, 0.68 mmol) and tetrahydrofuran/acetic acid/water (12 ml, 1:1:1) was stirred at room temperature overnight. The mixture was diluted with ethyl ether and washed thoroughly with sodium bicarbonate solution, water and brine. Evaporation of the dried (magnesium sulfate) organic phase gave the title furan. IR(CHCl$_3$): 3400 and 1735. $^1$HNMR(CDCl$_3$): 0.73 (q, 6H, J=6.8 Hz), 0.85 (t, 3H, J=6.8 Hz), 0.92 (t, 9H, J=7.8 Hz), 1.24 (br s, 16H), 1.58 (m, 3H), 1.75 (p, 2H, J=5.4 Hz), 2.31 (t, 2H, J=9.0 Hz), 3.16 (m, 2H), 3.36 (dd, 1H, J=14.8 Hz, 3.6 Hz), 3.60 (dd, 1H, J=14.8 Hz, 9.0 Hz), 3.69 (t, 2H, J=5.7 Hz), 5.38 (t, 1H, J=6.1 Hz), 6.26 (dd, 1H, J=9.0 Hz, 3.6 Hz), 6.57 (s, 1H) and 7.66 (s, 1H). $^{13}$CNMR(CDCl$_3$): 2.9, 7.1, 13.9, 22.5, 24.6, 28.9, 29.0, 29.1, 29.2, 29.3, 29.5, 31.8, 32.1, 34.2, 40.5, 55.7, 59.7, 63.1, 118.8, 122.6, 144.7, 160.2 and 173.0. LRMS (m/e % abundance) 545(m$^+$, 1), 516(5), 459(10), 408(32), 407(100), 316(29), 285(19), 252(1), 226(18), 225(85), 224(40), 200(15), 183(61), 179(48), 151(30), 115(47) and 73(83).

4-[1-Dodecanoyloxy-2-N-(3-hydroxypropyl)sulfonamido]ethyl-5-hydroxy-2(5H)-furanone (Compound 8)

A mixture of 4-[1-dodecanoyloxy-2-N-(3-hydroxypropyl)sulfonamidoethyl-2-triethylsilylfuran (Compound 34, 105 mg, 0.19 mmol), water (5 drops) and Rose Bengal (ca. 0.5 mg) in tetrahydrofuran (20 ml) was exposed to singlet oxygen at 0° C. for 5 hours. The residue, after removal of the solvent was purified by flash chromatography on silica using 70% ethyl acetate/hexane to give the title furanone. IR(CHCl$_3$): 3400 and 1770. $^1$HNMR(CDCl$_3$): 0.88 (t, 3H, J=6.8 Hz), 1.28 (m, 16H), 1.58 (br m, 2H), 1.79 (br m, 2H), 2.42 (t, 2H, J=7.6 Hz), 3.25 (m, 2H), 3.55 (m, 1H), 3.74 (br t, 2H), 5.63 (br t, 1H), 6.05 (br s, 1H), 6.16 (s, 1H), 6.26 (s, 1H), and 6.52 (br s, 1H). $^{13}$CNMR(CDCl$_3$): 13.8, 22.5, 28.9, 29.0, 29.1, 29.3, 29.4, 31.7, 33.8, 40.5, 53.2, 59.9, 64.3, 97.9, 98.0, 120.6, 163.9, 170.5 and 173.3. LRMS (m/e, % abundance) 463 (M$^+$, 6), 281(29), 264(37), 258(43), 246(48), 218(48), 200(19), 183(37), 156(39), 76(100) and 69(11).

Example 11

4-[1-Dodecanoyloxy-2-N-(3-carboxyethyl)sulfonamido]ethyl-2-triethylsilylfuran (Compound 35)

Jones' Reagent (0.57 mmol; 0.22 ml of a 2.59M solution) was added to a solution of 4-[1-dodecanoyloxy-2-N-(3-hydroxypropyl)sulfonamide]ethyl-2-triethylsilylfuran (Compound 34, 207 mg, 0.38 mmol) in acetone (10 ml) at room temperature. After 10 minutes, the mixture was diluted with water and extracted with ethyl acetate. Evaporation of the dried (magnesium sulfate) extracts gave an oil, which was purified by flash chromatography on silica using ethyl acetate containing 0.2% acetic acid to give the title furan. IR(CHCl$_3$): 3200, 1730 and 1780. $^1$HNMR(CDCl$_3$): 0.72 (q, 6H, J=6.8 Hz), 0.85 (t, 3H, J=6.8 Hz), 0.94 (t, 9H, J=7.8 Hz), 1.25 (br s, 16H), 1.60 (m, 2H), 2.35 (m, 2H), 2.67 (t, 2H, J=6.0 Hz), 3.35 (br t, 2H), 3.40 (dd, 1H, J=14.8 Hz, 3.5 Hz), 3.63 (dd, 1H, J=14.8 Hz, 9.2 Hz), 5.59 (t, 1H, J=6.4

Hz), 6.29 (dd, 1H, J=9.2 Hz, 3.5 Hz), 6.56 (s, 1H), and 7.65 (s, 1H). $^{13}$CNMR(CDCl$_3$): 2.8, 6.9, 13.8, 22.4, 24.4, 24.5, 28.8, 29.0, 29.1, 29.2, 29.4, 31.7, 34.1, 34.5, 38.3, 56.3, 63.1, 119.0, 122.7, 145.1, 160.8, 173.5 and 176.7. LRMS (m/e, % abundance) 577[(M+NH$_4$)+ 30], 560 (M+ +1, 7), 491(12), 474(57), 444(30), 431(6), 407(94), 377(37), 360(18), 296(100), 225(49), 183(26), 132(25) and 90(35).

4-[1-Dodecanoyloxy-2-N-(3-carboxyethyl)sulfonamido]ethyl-5-hydroxy-2(5)-furanone (Compound 9)

A mixture of 4-[1-dodecanoyloxy-2-N-(3-carboxyethyl)sulfonamido]ethyl-2-triethylsilylfuran (Compound 35, 119 mg, 0.21 mmol), Rose Bengal (5 mg) and water (10 drops) in tetrahydrofuran (20 ml) was exposed to singlet oxygen at 0° C. for 6 hours. The residue, after solvent removal, was purified by flash chromatography on silica using 10% methanol/chloroform containing 0.2% acetic acid top give the title furanone. IR(CHCl$_3$): 3400 and 1750. $^1$HNMR(CDCl$_3$): 0.84 (t, 3H, J=6.6 Hz), 1.27 (br s 16H), 1.59 (m, 2H), 2.38 (br t, 2H), 2.62 (br m, 2H), 3.59 (br m, 2H), 3.60 (br m, 2H), 5.82 (br t, 1H), 6.02 (br d, 1H), 6.14 (s, 1H), 6.24 (br s, 1H) and 7.60 (br s, 1H) $^{13}$CNMR(CDCl$_3$): 13.8, 22.5, 24.4, 28.9, 29.1, 29.2, 29.3, 29.5, 31.7, 33.8, 34.4, 38.5, 53.5, 64.1, 98.0, 120.7, 163.9, 170.8, 170.9, 173.5 and 176.2.

Example 12

4-[1-Dodecanoyloxy-2-N-(3-diethylphosphonopropyl)-sulfonamido]ethyl-2-triethylsilyfuran (Compound 36)

Triethylamine (68 ul, 0.49 mmol), followed by diethyl chlorophosphate (35 ul, 0.25 mmol) was added to a solution of 4-[1-dodecanoyloxy-2-N-(3-hydroxypropyl)sulfonamido]ethyl-2-triethylsilylfuran (Compound 34, 121 mg, 0.22 mmol) in tetrahydrofuran (2 ml) at 0°. After stirring at room temperature for 15 hours, the mixture was quenched with water and extracted with ethyl ether. Evaporation of the dried (magnesium sulfate) extracts gave an oil, which was purified on a silica column using 40% ethyl acetate/hexane to give the title furan. IR(CHCl$_3$): 1730, 1220, 1160, 1040. $^1$HNMR(CDCl$_3$): 0.68 (q, 6H, J=7.8 Hz), 0.81 (t, 3H, J=6.6 Hz), 0.91 (t, 9H, J=7.7 Hz), 1.17 (br s, 16H), 1.28 (t, 6H, J=7.1 Hz), 1.53 (m, 2H), 1.85 (p, 2H, J=6.3 Hz), 2.27 (dt, 2H, J=7.5 Hz, 3.2 Hz), 3.18 (dt, 2; H, J=6.5 Hz, 6.5 Hz), 3.33 (dd, 1H, J=14.7 Hz, 3.6 Hz), 3.58 (dd, 1H, J= 14.7 Hz, 9.1 Hz), 4.08 (m, 6H), 5.14 (t, 1H, J=6.2 Hz), 6.25 (dd, 1H, J=9.1 Hz, 3.6 Hz), 6.54 (s, 1H) and 7.63 (s, 1H). $^{13}$CNMR(CDCl$_3$): 6.9, 13.8, 15.7, 15.8, 22.4, 24.4, 28.8, 29.0, 29.2, 29.3, 30.8, 30.9, 31.6, 34.1, 39.3, 56.1, 63.0, 63.8, 63.9, 64.2, 64.3, 119.1, 122.9, 145.0, 160.5 and 173.2. LRMS (m/e % abundance): 681(M+, 0.2), 652(34), 482(100), 452(8), 417(58), 328(21), 183(19), 155(13), 99(16) and 87(11).

4-[1-Dodecanoyloxy-2-N-(3-diethylphosphonopropyl)-sulfonamido]ethyl-5-hydroxy-2(5H)-furanone (Compound 10)

4-[1-Dodecanoyloxy-2-N-(3-diethylphosphonopropyl)sulfonamido]ethyl-2-triethylsilylfuran (Compound 36) is oxidized with singlet oxygen under similar conditions as in Example 1, to give 4-[1-dodecanoyloxy-2-N-(3-diethylphosphonopropyl)sulfonamido]ethyl-5-hydroxy-2(5H)-furanone (Compound 10).

Example 13

4-[1-Dodecanoyloxy-2-N-(3-phosphonopropyl)sulfonamido]ethyl-5-hydroxy-2(5H)-furanone (Compound 11)

4-[1-Dodecanoyloxy-2-N-(3-diethylphosphonopropyl)sulfonamido]ethyl-2-triethylsilylfuran (Compound 36) is reacted with bromotrimethylsilane to give 4-[1-dodecanoyloxy-N-(3-phosphonopropyl)sulfonamido]ethyl-2-triethylsilylfuran. Oxidizing this intermediate with singlet oxygen in the presence of Rose Bengal, under similar conditions as in Example 1, gives the title furanone.

Example 14

N-(2-Dimethylaminoethyl)methanesulfonamide (Compound 37)

Methanesulfonyl chloride (Compound 19, 2.6 ml, 34.0 mmol) was added to a mixture of N,N-dimethylethylenediamine (3.7 ml, 34.0 mmol) and diisopropylethylamine (5.93 ml, 34.0 mmol) in tetrahydrofuran (30 ml) at 0° C. After 1.5 hours stirring at 0°, the mixture was quenched with water and extracted thoroughly with ethyl acetate. Evaporation of the dried (magnesium sulfate) extract gave an oil, which was purified by flash chromatography on silica using 20% methanol/chloroform to give the title sulfonamide. $^1$HNMR(CDCl$_3$): 2.24 (s, 6H), 2.48 (t, 2H, J=5.9 Hz), 2.97 (s, 3H), 3.18 (t, 2H, J=5.6 Hz). $^{13}$CNMR(CDCl$_3$): 39.3, 39.9, 44.5 and 57.8.

4-[1-Hydroxy-2-N-(3-dimethylaminoethyl)sulfonamido]ethyl-2-triethylsilylfuran (Compound 38)

N-(2-Dimethylaminoethyl)methanesulfonamide (Compound 37, 410 mg, 2.5 mmol) was added to a solution of lithium diisopropylamide (5.0 mmol) at 0° C. under argon. After 1 hour, a solution of 2-triethylsilyl-4-furaldehyde (Compound 18, 500 mg, 2.38 mmol) in tetrahydrofuran (3 ml) was added. Stirring was continued at room temperature for 14 hours, then the reaction was quenched with water. Extraction (ethyl acetate) and evaporation of the dried (magnesium sulfate) extracts gave an oil, which was purified on a silica column eluted with 5% methanol/chloroform to give the title furan. $^1$HNMR(CDCl$_3$): 0.76 (q, 6H, J=8.0 Hz), 0.97 (t, 9H, J=8.0 Hz), 2.26 (s, 6H), 2.50 (m, 2H), 3.30 (t, 2H, J=5.6 Hz), 3.37 (t, 2H, J=4.6 Hz), 5.23 (dd, 1H, J=7.4 Hz, 4.5 Hz), 6.59 (s, 1H), and 7.62 (s, 1H).

4-[1-Dodecanoyloxy-2-N-(3-dimethylaminoethyl)sulfonamido]ethyl-5-hydroxy-2(5H)furanone (Compound 12)

4-[1-Hydroxy-2-N-(3-dimethylaminoethyl)sulfonamido]ethyl-2-triethylsilylfuran (Compound 38) is reacted with dodecanoyl chloride and triethylamine to give 4-[1-dodecanoyloxy-2-N-(3-dimethylaminoethyl)-sulfonamido]ethyl-2-triethylsihylfuran. Oxidizing this intermediate with singlet oxygen, under similar conditions as in Example 1, gives the title furanone.

Example 15

4-[1-Dodecanoyloxy-2-N-(4-carboxyphenyl)sulfonamido]ethyl-5-hydroxy-2(5H)-furanone (Compound 13)

4-Aminobenzoic acid is reacted with methanesulfonyl chloride (Compound 19) to give N-(4-carboxyphenyl)methanesulfonamide. 2-Triethylsilyl-4-furaldehyde (Compound 18) is reacted with N-(4-carboxyphenyl)methanesulfonamide and lithium diisopropylamide. The resulting 4-[1-hydroxy-2-N-(4-carboxyphenyl)sulfonamido]-ethyl-2-triethylsilylfuran is esterified with dodecanoyl chloride in the presence of triethylamine. Oxidizing this ester with singlet oxygen, under conditions as in Example 1, gives the title furanone.

Biological Activity

In the above-described phospholipase $A_2$ assay the compounds of the invention were found to provide 50% inhibition ($IC_{50}$) of bee venom phospholipase $A_2$ at the following concentrations (in micromoles), as indicated in Table 1.

TABLE 1

| Phospholipase $A_2$ Assay. | |
|---|---|
| Compound name or number | $IC_{50}$ (um) |
| 1* | 0.03 |
| 4 | 0.04 |
| 5 | 0.1 |
| 6 | 0.05 |
| 7 | 0.05 |

*Data for Compound 1 (monoalide) are provided for comparison.

What is claimed is:

1. Compounds of the formula

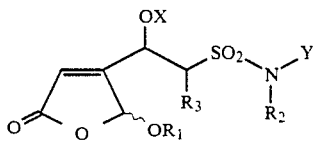

where $R_1$ is H or alkyl of 1 to 20 carbons, CO—$R_1$* CO—O—$R_1$* CO—NH—$R_1$* or PO(O$R_1$*)$_2$ or PO(O$R_1$*)$R_1$* where $R_1$* independently is H, alkyl of 1 to 20 carbons, or phenyl;

$R_2$ is H, alkyl or 1 to 20 carbons;

$R_3$ is H or alkyl or 1 to 20 carbons;

X is H, $R_4$, CO—$R_4$, CO—O—$R_4$, CO—NH—$R_4$, CO—N—($R_4$)$_2$, PO(O$R_4$)$_2$ or PO(O$R_4$)$R_4$, and $R_4$ independently is H, phenyl, alkyl of 1 to 20 carbons or is alkyl or 1 to 20 carbons substituted with a hydroxyl, alkoxy, amino, thioalkoxy, with a O—CO$R_4$* group or with a CO$R_4$* group where $R_4$* is H, lower alkyl, Oh, O$R_4$, NH$_2$, NHR$_4$ or N($R_4$)$_2$ group where $R_4$ independently is H or lower alkyl, with the proviso that when X is CO—O—$R_4$ or is CO—NH—$R_4$ then $R_4$ is not hydrogen, and Y is H, phenyl or carboxy substituted phenyl, or alkyl of 1 to 20 carbons, or is alkyl of 1 to 20 carbons substituted with a hydroxyl, alkoxy, dimethyl substituted amino, thioalkoxy, O—PO(O$R_5$)$_2$, O—PO(O$R_5$)$R_5$, O—SO$_3$H, O—SO$_2$$R_5$, O—CO$R_5$, or CO$R_5$ group where $R_5$ is H, lower alkyl, OH, O$R_5$*, NH$_2$, NHR$_5$* or N($R_5$*)$_2$ group where $R_5$* is lower alkyl, with the proviso that when Y is an alkyl substituted with O—PO(O$R_5$)$_2$ or with O—PO(O$R_5$)$R_5$ then $R_5$ is not OH, and salts of said compounds.

2. Compounds of claim 1 where $R_1$ is hydrogen or acyl.

3. Compounds of claim 2 where $R_1$ is acetyl.

4. Compounds of claim 1 where $R_3$ is hydrogen.

5. Compounds of claim 1 where $R_2$ is hydrogen.

6. Compounds of claim 1 where Y is straight chain alkyl of 6 to 20 carbons, straight chain alkyl terminally substituted with hydroxyl, dialkylamino, carboxy group or with a O—PO(O$R_5$)$_2$ group where $R_5$ is alkyl or hydroxyl.

7. Compounds of claim 1 where Y is phenyl or carboxy substituted phenyl.

8. Compounds of claim 1 where X is hydrogen.

9. Compounds of claim 1 where X is CO—$R_4$ and $R_4$ is a straight chain alkyl group.

10. Compounds of claim 1 where X is CO—$R_4$ and $R_4$ is a straight chain alkyl group terminally substituted with a CO$R_4$* group where $R_4$* is lower alkyl, OH, or O$R_4$ where $R_4$ is alkyl.

11. Compounds of claim 1 where X is CO—NH—$R_4$.

12. Compounds of claim 11 where $R_4$ is phenyl.

13. Compounds of the formula

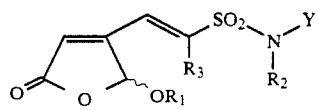

where $R_1$ is H or alkyl or 1 to 20 carbons, CO—$R_1$* CO—O—$R_1$* CO—NH—$R_1$* or PO(O$R_1$*)$_2$ or PO(O$R_1$*)$R_1$* where $R_1$* independently is H, alkyl of 1 to 20 carbons;

$R_2$ is H, alkyl or 1 to 20 carbons;

$R_3$ is H or alkyl or 1 to 20 carbons, and

Y is H, phenyl or carboxy substituted phenyl, or alkyl or 1 to 20 carbons, or is alkyl of 1 to 20 carbons substituted with a hydroxyl, alkoxy, dimethyl substituted amino, thioalkoxy, O—PO(O$R_5$)$_2$, O—PO(O$R_5$)$R_5$, O—SO$_3$H, O—SO$_2$$R_5$, O—CO$R_5$, or CO$R_5$ group where $R_5$ is H, lower alkyl, OH, O$R_5$*, NH$_2$, NHR$_5$* or N($R_5$*)$_2$ group where $R_5$* is lower alkyl, with the proviso that when Y is an alkyl substituted with O—PO(O$R_5$)$_2$ or with O—PO(O$R_5$)$R_5$ then $R_5$ is not OH, and salts of said compounds.

14. Compounds of claim 13 where $R_1$ is hydrogen or acyl.

15. Compounds of claim 14 where $R_1$ is acetyl.

16. Compounds of claim 13 where $R_3$ is hydrogen.

17. Compounds of claim 13 where $R_2$ is hydrogen.

18. Compounds of claim 13 where Y is straight chain alkyl of 6 to 20 carbons, straight chain alkyl terminally substituted with hydroxyl, dialkylamino, carboxy group or with a O—PO(O$R_5$)$_2$ group where $R_5$ is alkyl or hydroxyl.

19. Compounds of claim 13 where Y is phenyl or carboxy substituted phenyl.

20. Compounds of the formula

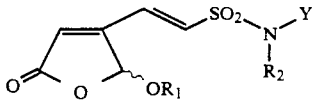

where $R_1$ is H or alkyl or 1 to 20 carbons, CO—$R_1$* CO—O—$R_1$* CO—NH—$R_1$* or PO(O$R_1$*)$_2$ or PO(O$R_1$*)$R_1$* where $R_1$* independently is H, alkyl of 1 to 20 carbons, phenyl;

$R_2$ is H, and

Y is H, phenyl or carboxy substituted phenyl, or alkyl of 1 to 20 carbons, or is alkyl or 1 to 20 carbons substituted with a hydroxyl, alkoxy, dimethyl substituted amino, O—PO(OR$_5$)$_2$, O—PO(OR$_5$)R$_5$, O—COR$_5$, or COR$_5$ group where R$_5$ is H, lower alkyl, OH, OR$_5$*, NH$_2$, NHR$_5$* or N(R$_5$*)$_2$ group where R$_5$* is lower alkyl, with the proviso that when Y is an alkyl substituted with O—PO(OR$_5$)$_2$ or with O—PO(OR$_5$)R$_5$ then R$_5$ is not OH, and salts of said compounds.

21. Compounds of claim 20 where Y is straight chain alkyl of 6 to 20 carbons.

22. Compounds of claim 21 where Y is CH$_3$(CH$_2$)$_{11}$.

23. The compound of claim 22 where R$_1$ is hydrogen.

24. Compounds of the formula

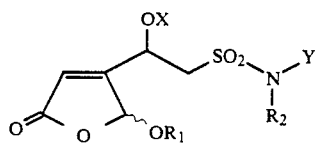

where R$_1$ is H or alkyl or 1 to 20 carbons, CO—R$_1$* CO—O—R$_1$* CO—NH—R$_1$* or PO(OR$_1$*)$_2$ or PO(OR$_1$*)R$_1$* where R$_1$* where R$_1$* independently is H, alkyl of 1 to 20 carbons, phenyl;

R$_2$ is H;

X is H, CO—R$_4$, CO—NH—R$_4$, or CO—N—(R$_4$)$_2$, and R$_4$ independently is H, phenyl, alkyl of 1 to 20 carbons or is alkyl of 1 to 20 carbons substituted with COR$_4$* group where R$_4$* is OH, OR$_4$, NH$_2$, NHR$_4$ or N(R$_4$)$_2$ group where R$_4$ independently is H or lower alkyl, with the proviso that when X is CO—NH—R$_4$ then R$_4$ is not hydrogen, and Y is H, phenyl or carboxy substituted phenyl, or alkyl or 1 to 20 carbons, or is alkyl or 1 to 20 carbons substituted with a hydroxyl, alkoxy, dimethyl substituted amino, O—PO(OR$_5$)$_2$, O—PO(OR$_5$)R$_5$, O—COR$_5$, or COR$_5$ group where R$_5$ is H, lower alkyl, OH, OR$_5$*, NH$_2$, NHR$_5$* or N(R$_5$*)$_2$ group where R$_5$* is lower alkyl, with the proviso that when Y is an alkyl substituted with O—PO(OR$_5$)$_2$ or with O—PO(OR$_5$)R$_5$ then R$_5$ is not OH, and salts of said compounds.

25. Compounds of claim 24 where Y is CH$_3$(CH$_2$)$_{11}$ and R$_2$ is hydrogen.

26. Compounds of claim 25 where X is hydrogen.

27. The compound of claim 26 where R$_1$ is hydrogen.

28. Compounds of claim 25 where X is CH$_3$CO.

29. The compound of claim 32 where R$_1$ is hydrogen.

30. Compounds of claim 25 where X is CO(CH$_2$)$_3$COOH.

31. The compound of claim 30 where R$_1$ is hydrogen.

32. Compounds of claim 24 where Y is (CH$_2$)$_3$OH.

33. Compounds of claim 32 where X is CO(CH$_2$)$_{10}$CH$_3$.

34. The compound of claim 33 where R$_1$ is hydrogen.

35. Compounds of claim 24 where Y is (CH$_2$)$_2$COOH.

36. Compounds of claim 35 where X is CO(CH$_2$)$_{10}$CH$_3$.

37. The compound of claim 36 where R$_1$ is hydrogen.

38. Compounds of claim 24 where Y is (CH$_2$)$_3$OPO(OEt)$_2$.

39. Compounds of claim 38 where X is CO(CH$_2$)$_{10}$CH$_3$.

40. The compound of claim 39 where R$_1$ is hydrogen.

41. Compounds of claim 24 where Y is (CH$_2$)$_3$OPO(OH)$_2$.

42. Compounds of claim 41 where X is CO(CH$_2$)$_{10}$CH$_3$.

43. The compound of claim 42 where R$_1$ is hydrogen.

44. Compounds of claim 24 where Y is C$_6$H$_5$-para-COOH.

45. Compounds of claim 44 where X is CO(CH$_2$)$_{10}$CH$_3$.

46. The compound of claim 45 where R$_1$ is hydrogen.

* * * * *

UNITED STATES PATENT AND TRADEMARK OFFICE
CERTIFICATE OF CORRECTION

Page 1 of 2

PATENT NO. : 5,081,261
DATED : January 14, 1992
INVENTOR(S) : Gary C. M. Lee

It is certified that error appears in the above-indentified patent and that said Letters Patent is hereby corrected as shown below:

Column 2, line 14, delete "of" (second occurrence); and
Column 2, line 19, "U.S. Pat.:" should be --U.S. Patents--.

Column 4, line 22, "defines" should be --defined--;

Column 4, line 29, "or" should be --of--;

Column 5, line 32, "aliphatic-cycle" should be --aliphatic-cyclic--;

Column 6, line 42, "CORgroup" should be --$COR_5$ group--;

Column 8, line 27, "administration" should be --administered--;

Column 9, line 16, "dexrose," should be --dextrose,--;

Column 9, line 39, "mm" should be --min--;

Column 11, lines 4-5, after "Formula 10" insert --in the presence--;

Column 17, line 16, change "$C_{26}H_{40}NO_4SSi(M^+)$" to --$C_{26}H_{49}NO_5SSi^+$)--;

Column 17, line 61, "4-[2-(n-"... should be --4-[2-N- --...;

Column 17, line 62, "0.098" should be --0.08--;

Column 18, line 34, "Gluraroyloxy"... should be --Glutaroyloxy--...;

Column 18, line 51, after "64.7," insert --64.8,--;

Column 19, line 34, "oxide" should be --oxygen--;

Column 19, line 62, ..."2-(5H)"... should be ...--2(5H)--...;

Column 19, line 67, "single" should be --singlet--;

Column 20, line 6, "7.89" should be --7.8--;

Column 20, line 8, "29.9" should be --29.2--;

Column 20, line 33, ..."2-(5H)"... should be ...--2(5H)--...;

Column 22, line 24, "252(1)," should be --252(11),--;

UNITED STATES PATENT AND TRADEMARK OFFICE
CERTIFICATE OF CORRECTION

PATENT NO. : 5,081,261
DATED : January 14, 1992
INVENTOR(S) : Gary C. M. Lee

It is certified that error appears in the above-indentified patent and that said Letters Patent is hereby corrected as shown below:

Column 22, line 56, ..."sulfonamide]"... should be ...—sulfonamido]—...;

Column 22, line 68, "1; H," should be —1H,—;

Column 23, line 21, "top" should be —to—;

Column 25, line 40, Claim 1, "or" should be —of—;

Column 25, line 41, Claim 1, "or" should be —of—;

Column 25, line 44, Claim 1, "phenyl,alkyl" should be —phenyl, alkyl—;

Column 25, line 45, Claim 1, "or" (second occurrence) should be —of—;

Column 25, line 48, Claim 1, "Oh," should be —OH—;

Signed and Sealed this

Eleventh Day of January, 1994

Attest:

BRUCE LEHMAN

*Attesting Officer*   *Commissioner of Patents and Trademarks*